United States Patent [19]

Nakano

[11] 4,333,464
[45] Jun. 8, 1982

[54] SANITARY NAPKIN

[75] Inventor: Tadao Nakano, Kainan, Japan

[73] Assignee: Zenmi Co., Ltd., Wakayama, Japan

[21] Appl. No.: 139,266

[22] Filed: Apr. 11, 1980

[30] Foreign Application Priority Data

Apr. 28, 1979 [JP] Japan .................. 54-53078

[51] Int. Cl.³ ............................ A61F 13/16
[52] U.S. Cl. .................. 128/290 R; 128/284;
128/287; 428/407; 428/533; 428/532; 428/516;
428/520; 428/519; 428/689; 428/697
[58] Field of Search .................. 128/284, 287, 290 R;
428/407, 689, 327, 697, 532, 533, 516, 519, 520

[56] References Cited

U.S. PATENT DOCUMENTS 3,903,889 9/1975 Torr ..................................... 128/287
3,952,347 4/1976 Comerford et al. ............. 128/284 X
4,055,184 10/1977 Karami ........................... 128/284 X

FOREIGN PATENT DOCUMENTS 2904634 9/1979 Fed. Rep. of Germany ...... 128/287
49-44318 of 1974 Japan.

Primary Examiner—P. Ives
Attorney, Agent, or Firm—Wegner & Bretschneider

[57] ABSTRACT

Sanitary napkin comprising at least a layer consisting of a water-absorbing substance containing a powdery polymer which is soluble in water or is dispersible in water and is highly water-absorbable and at least a film based on polyvinyl alcohol, which is soluble in water or is dispersible in water is disclosed, the napkin being excellent in absorbing and holding the menstrual blood, in preventing the exudation and the leakage of the menstrural blood once absorbed therein and in disintegrating in water.

3 Claims, 8 Drawing Figures

SANITARY NAPKIN

BACKGROUND OF THE INVENTION

The present invention concerns a sanitary napkin excellent in absorbing and holding the menstrural blood and in preventing the exudation and the leakage of the menstrural blood once absorbed therein as well as excellent in disintegrating in water.

The performances required to a sanitary napkin are (1) an ability of absorbing and holding the menstrural blood in a large amount (excellent in absorbing and holding), (2) an ability of preventing the exudation and the leakage of the menstrural blood once absorbed therein (excellent in preventing the exudation and the leakage of once absorbed blood) and (3) a property of collapsing in water by disintegration and dispersion in water (collapsing property in water) not to cause the clogging of the drain-pipe and the disturbance of the function of the purifier of excreta when the napkin is thrown into the stool in a flush toilet including the purifier of excreta.

However, the hitherto proposed or practiced sanitary napkins do not necessarily fulfill all the performances (1) to (3) above-mentioned.

For example, hitherto a sanitary napkin comprising covering an absorbing layer of the menstrural blood formed of a mixture of crushed pulp and sanitary cotton and lined with a pile of a sheet of water-proof paper and a water-proof film consisting of low-density polyethylene with a non-woven cloth which is dispersible in water, or another sanitary napkin (Japanese Utility Model Publications 44318/74, 44319/74 and 44000/75) comprising covering the above-mentioned absorbing layer of the menstrural blood lined with the sheet of waterproof paper and a film containing more than 50% by weight of polyvinyl alcohol of an average degree of saponification of 89.5 to 98.5 mol% with a covering material dispersible into water in the presence of an aqueous solution of polyvinyl alcohol has been proposed, however, since these conventional sanitary napkins do not absorb a large amount of the blood and do not sufficiently prevent the exudation and the leakage of the once absorbed blood, they are not satisfactorily practicized.

Accordingly, the purpose of the present invention is to offer a sanitary napkin excellent in absorbing and holding the menstrural blood and also excellent in preventing the exudation and the leakage of the once absorbed blood as well as excellent in disintegrating in water.

DETAILED DESCRIPTION OF THE INVENTION

Figure 1:
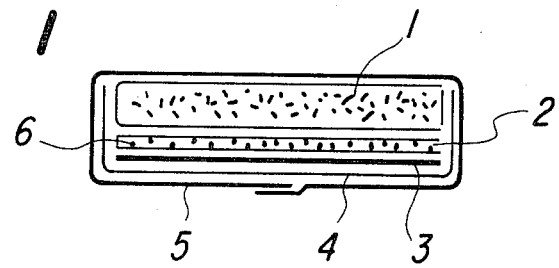
FIGS. 1 to 7 of the drawing are the exemplification of the structure of the sanitary napkin of the present invention.

The characteristics aspect of the present invention is to improve remarkably the amount of menstrural blood absorbed and held in a sanitary napkin and to extremely effectively prevent the exudation and the leakage of the blood once absorbed into the sanitary napkin by the combined use of a thin layer of a water-absorbing substance containing a water-soluble or water-dispersible and highly water-absorbing powdery polymer as a layer for absorbing and holding the blood and of a film based on polyvinyl alcohol, particularly of the polyvinyl alcohol of an average degree of saponification of 75 to 98 mol% as a leakage-proof film for preventing the exudation and the leakage of the blood once absorbed in the above-mentioned layer.

Another characteristic aspect of the present invention is, by making the above-mentioned absorbing and holding layer include a gelification-accelerator of polyvinyl alcohol, to bring the leakage-preventing film into contact with the moisture in the absorbed blood in the absorbing and holding layer to be moistured resulting in the formation of a water-insoluble gel temporally so as to exhibit an extremely high preventing effect against the exudation and the leakage of the blood absorbed in the absorbing and holding layer.

The following description is the more detailed explanation of the present invention.

The structural characteristic of the sanitary napkin of the present invention is that the napkin includes at least a layer comprising a water-dispersible and water-absorbing substance uniformly containing of a powdery polymer which is water-soluble or water-dispersible and highly water-absorbable or a mixture of the above-mentioned powdery polymer and a powdery gelification-accelerator for polyvinyl alcohol, and at least a leakage-preventing film for the blood based on polyvinyl alcohol, which lines the undersurface of the above-mentioned layer.

The above-mentioned highly water-absorbing powdery polymer for use in the present invention includes starch, processed starch, cross-linked starch, starch grafted with acrylic monomer such as $\beta$-hydroxyethylacrylate, acrylonitrile, acrylic acid and acrylamide, carboxymethylcellulose, cross-linked carboxymethylcellulose, hydrophilic copolymer(s) of acrylates, for example, polyacrylic acid and polyacrylamide, polyethylene oxide, cross-linked polyethylene oxide, copolymers of a vinyl ester and an ethylenically unsaturated carboxylic acid and their saponification products, for example, copolymer of vinylacetate and acrylic acid and its saponification product, polyvinyl alcohol and its derivatives and derivatives of cellulose. The above-mentioned polymers may be used as a mixture of more than two species.

In order to make the layer comprising a water-dispersible substance uniformly containing the above-mentioned powdery polymer, at first, a thin layer is formed by uniformly scattering the above-mentioned powder of the polymer on a water-absorbing membranous substance such as a sheet of water-absorbing paper consisting of crushed pulp and a non-woven cloth consisting of rayon and then after covering the thin layer with the above-mentioned sheet of water-absorbing paper or the non-woven cloth, the above-mentioned powder of the polymer is solidified between the above-mentioned sheets or the above-mentioned non-woven cloths by applying heat or pressure thereonto. In another way an uniform mixture of a water-absorbing substance such as crushed pulp and the above-mentioned powder of the polymer may be processed into a pile having a predetermined thickness. In any case, the amount of the polymer used for the above-mentioned layer is prefereably 0.1 to 5 g per piece of sanitary paper weighing about 7 to 10 g.

The piled material obtained by the above-mentioned procedures and comprising the water-absorbing substance containing the above-mentioned powder of the polymer forms a swollen gel by rapidly absorbing water of 50 to 2,000 times of the weight of the above-mentioned polymer and accordingly, when the pile material is applied to a sanitary napkin, it absorbs the menstrural blood rapidly in a large amount and maintains the absorbed blood, and moreover, it exhibits a characteristic property that it does not exude the moisture in the once absorbed blood even it is pressed.

In addition, although there are some members insoluble in water among the above-mentioned polymers, since the polymer is included in the above-mentioned pile in a state of powder, it is dispersible when the pile is brought into water and accordingly, there are no disturbances after thrown into the stool of flush toilet.

The film based on polyvinyl alcohol for use in the present invention as a film for preventing the leakage of menstrural blood is possibly prepared by processing a mixture comprising the admixture of (1) polyvinyl alcohol, for example, glycerol, ethylene glycol, propylene glycol, triethylene glycol, polyethylene glycol, sorbitol as a plasticizer. (2) other water-soluble high polymeric substance, for example, starch, water-soluble starch, dextrin as a filler and (3) a surface active agent with polyvinyl alcohol of a degree of saponification of 75 to 98 mol% into a film of 0.01 to 0.5 mm in thickness.

The amounts of addition of the above-mentioned plasticizer, the filler and the surfactant to polyvinyl alcohol are preferably 10 to 30, 0 to 20 and 0.1 to 1% by weight, respectively, of the total weight of the mixture.

The leakage-preventing film thus obtained swells or half-dissolves by the moisture of the menstrural blood to form a gel layer, and the thus formed gel layer permeates the moisture of the blood, however, it does not permeate the pigment component of the blood, and accordingly, the exudation or the leakage of the blood is completely prevented in the external appearance without anxiety of getting one's lingeries dirty.

The present invention, as has been described before, includes an aspect of using a powdery gelification-accelerator for polyvinyl alcohol together with a powdery polymer in the formation of the absorbing and holding layer for the menstrural blood, and the gelification-accelerator accelerates the gelification of the above-mentioned leakage-preventing film by the moisture so much that a temporarily insoluble gel is formed to bring about the more powerful leakage-preventing effect. However, since the water-insoluble gelified substance formed from the above-mentioned leakage-preventing film by the above-mentioned gelification-accelerator returns to the water-soluble or water-dispersible state due to the reduction of the gelifying capability of the gelification-accelerator when the concentration of the gelification-accelerator is reduced by a large amount of water, no problem is caused even when the sanitary napkin is thrown away after its use.

The above-mentioned gelification-accelerator includes $H_3BO_3$, $Na_3BO_3$, $Na_2SO_4$, $MgSO_4$ and $Al_2(SO_4)_3$, and its amount in use is preferably 0.001 to 0.1 g per piece of the sanitary napkin weighting about 7 to 10 g.

In the present invention, it is possible not only to use the above-mentioned absorbing and holding layer for the menstrural blood and the above-mentioned leakage-preventing film but also to use in combination of the film comprising the other water-dispersible substance, for instance, an absorbing layer consisting of crushed pulp, another absorbing layer consisting of rayon, both for absorbing the menstrural blood, and moreover, a sheet of water-dispersible paper, with the above-mentioned layer and film, and furthermore, by the change of the above-mentioned combination, the sanitary napkin of the present invention may take various construction.

In addition, in the present invention, in order to maintain the shape of a sanitary napkin, the whole body of pile composed of the above-mentioned various layers and the film is covered by a non-woven cloth which is dispersible in water. The non-woven cloth used hitherto for covering the conventional sanitary napkin may be used for the above-mentioned purpose, however, it is preferable to use a non-woven cloth obtained by paper-making using a mixture prepared by admixing a water-soluble resin as a binder with a pulp containing short fibers of viscose rayon. Since the above-mentioned non-woven cloth favorably permeates the menstrural blood and its wet strength is relatively high while it is dispersible in water, it does not give any harm to the above-mentioned performances required to a sanitary napkin.

The followings are the exemplification of the possible constructions of which the sanitary napkin can take while referring to the drawings:

In FIG. 1, the layer comprising crushed pulp for absorbing the menstrural blood is shown by 1, and the absorbing and holding layer arranged on the under surface of the layer 1 for the blood is shown by 2. The layer 2 is prepared by at first forming a thin layer comprising powdery carboxymethylcellulose on a sheet of water-absorbing paper consisting of crushed pulp, covering the thus formed thin layer with another sheet of the above-mentioned water-absorbing paper and then by applying a pressure on the thus covered layers to make the whole laminate into the body. Particles of powdery carboxymethylcellulose contained in the absorbing and holding layer 2 are shown by 6.

In FIG. 1, the leakage-preventing film for the blood arranged on the under surface of the above-mentioned absorbing and holding layer 2 is shown by 3, the film being based on polyvinyl alcohol and being extremely thin. In FIG. 1, a sheet of processed paper prepared by treating a sheet of water-dispersible paper on its surface with a water-repelling substance to an extent not to harm its water-dispersibility is shown by 4. This sheet 4 has a supplementary role of preventing the leakage of the moisture of the blood out of the sanitary napkin. The covering made of a non-woven cloth for maintaining the shape of the napkin is shown by 5 in FIG. 1.

Figure 2:
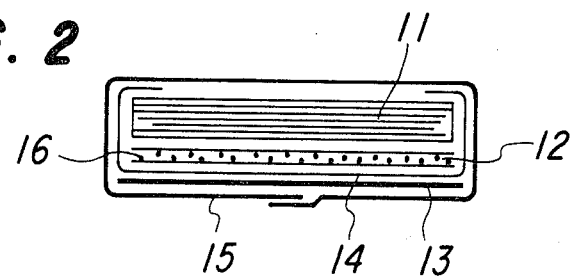
Figure 3:
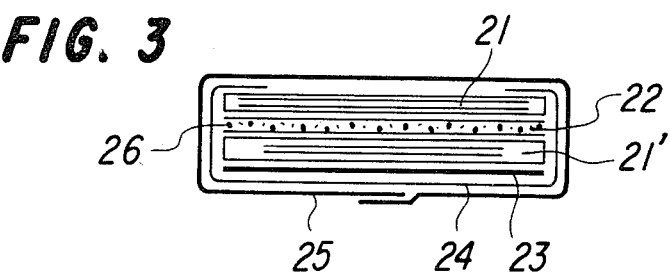

In FIG. 2, the absorbing layer for the blood, comprising a pile of papers manufactured from crushed pulp is shown by 11, the layer 12 being the blood-absorbing and holding layer, arranged on the under surface of the layer 11. The layer 12 has been prepared by the same procedures as in FIG. 1 except for using grafted starch with an acrylic monomer instead of carboxymethylcellulose (CMC). In FIG. 2, the water-dispersible sheet of processed paper arranged on the undersurface of the above-mentioned absorbing and holding layer 12, which has been shown in FIG. 3 is shown by 14. The leakage-preventing film for the blood arranged in the under surface of the sheet of processed paper 14 is shown by 13, the film 13 being based on polyvinyl alcohol. The non-woven cloth for covering the whole pile arranged as shown above is shown by 15. Particles of powdery grafted starch by an acrylic monomer contained in the absorbing and holding layer 12 are shown by 16.

In FIG. 3, the blood-absorbing layer comprising a pile prepared by crushed pulp is shown by 21, and the absorbing and holding layer for the blood arranged on the under surface of the layer 21 is shown by 22, the layer 22 having been prepared by the same procedures as in FIG. 1 except for using hydrophilic powdery grafted starch with acrylic monomer instead of CMC as powdery polymer. 21' shows the blood absorbing layer arranged on the under surface of the absorbing and holding layer 22, 21' being the same as 21. The leakage-preventing film for the blood, based on polyvinyl alcohol and arranged on the under surface of the above-mentioned absorbing layer 21' is shown by 23, and the sheet of processed paper dispersible in water, arranged on the under surface of the layer 22 is shown by 24, the sheet 24 being the same as in FIG. 1. The non-woven cloth for covering the whole piles arranged as shown above is indicated by 25. Particles of grafted starch with acrylic monomer included within the layer 22 are shown by 26.

Figure 4:
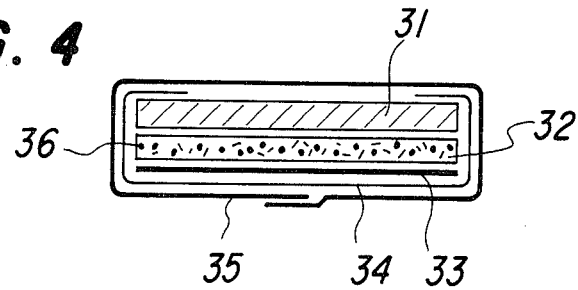

In FIG. 4, the blood-absorbing layer comprising crushed pulp is shown by 31, and the absorbing and holding layer for the blood, arranged on the under surface of the layer 31 is shown by 32, the layer 32 being the same as in FIG. 1. The leakage-preventing film for the blood, based on polyvinyl alcohol and arranged on the under surface of layer 32 is shown by 33, and the sheet of processed paper arranged on the under surface of the layer 33 is shown by 34, the layer 34 being the same as in FIG. 1. The covering comprising a non-woven cloth is shown by 35. Particles of powdery CMC contained in the layer 32 are shown by 36.

Figure 5:
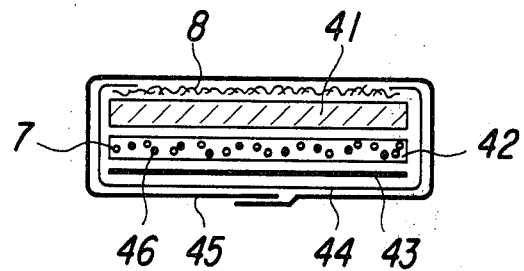

In FIG. 5, the blood-absorbing layer comprising crushed pulp is shown by 41. The layer of rayon arranged on the layer 41 is shown by 8, and the absorbing and holding layer for the blood, arranged on the under surface of the layer 41 and formed into a layer having a predetermined thickness from the mixture prepared by uniformly dispersing powdery CMC and powdery $H_3BO_3$ as a gelification accelerator of polyvinyl alcohol into crushed pulp is shown by 42. The leakage-preventing film for the blood, based on polyvinyl alcohol is shown by 43. In FIG. 5, the sheet of processed paper (the same as that in FIG. 1) arranged on the under surface of the film 43 is shown by 44, and the covering comprising a non-woven cloth is shown by 45. Particles of powdery CMC and those of powdery $H_3BO_3$, both of which have been dispersed in the absorbing and holding layer 42, are shown by 46 and 7, respectively.

Figure 6:
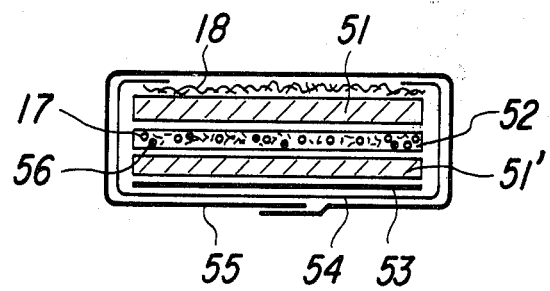

In FIG. 6, the absorbing layer for the menstrural blood, comprising crushed pulp is shown by 51, and the layer arranged on the upper surface of the layer 51, comprising rayon is shown by 18. The absorbing and holding layer for the blood arranged on the under surface of the layer 51 is shown by 52, the layer 52 being the same as in FIG. 5. The layer arranged on the under surface of layer 52 and is of the same structure as the layer 51 is another absorbing and holding layer for the blood and it is shown by 51'. The film 53 is the leakage-preventing film for the blood based on polyvinyl alcohol arranged on the under surface of the layer 51'.

The sheet of processed paper 54 is the same as that in FIG. 1 and the covering 55 is manufactured from a non-woven cloth.

Figure 7:
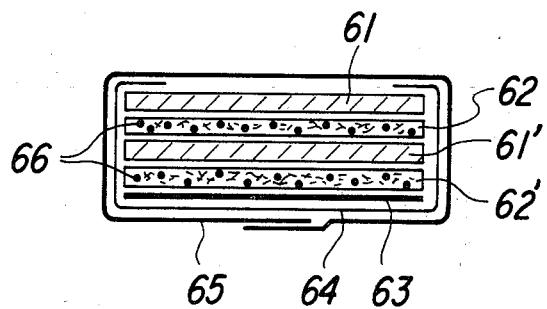

In FIG. 7, the absorbing layer for the blood, comprising crushed pulp is shown by 61. The absorbing and holding layer 62 for the blood is arranged on the under surface of the layer 61, the layer 62 being shaped to a layer having a predetermined thickness comprising a mixture of crushed pulp and cross-linked starch dispersed in the pulp. The layer 61' is the same as the above-mentioned layer 61 for absorbing the blood. Also the layer 62' is the same as the above-mentioned layer 62 for absorbing and holding the blood. The leakage-preventing film 63 for the blood is arranged on the under surface of the layer 42', and based on polyvinyl alcohol. The sheet 64 is the same as that in FIG. 1 and is of processed paper. The covering 65 comprises a non-woven cloth. Particles of cross-linked starch included in the layers 62 and 62' are shown by 66.

As will be understood from the above-exemplified construction of each component of the sanitary napkin according to the present invention, since the sanitary napkin according to the present invention includes a layer containing a powdery polymer with a high water absorbing capability and also a film based on polyvinyl alcohol capable of preventing the exudation and the leakage of the blood, and since all the materials composing the sanitary napkin are water-soluble or water-dispersible, the napkin is extremely excellent in absorbing and holding of, in preventing the exudation and leakage of the menstrural blood, and also in self-disintegrating property.

The followings are the exemplification of the present invention while referring to Examples not restricting the scope of the present invention.

EXAMPLE 1

As is shown in FIG. 1, (1) a layer 1 for absorbing the menstrural blood having a thickness of 4 mm and comprising crushed pulp, (2) a layer 2 for absorbing and holding the blood, obtained by applying a pressure to the pile consisting two sheets of water-absorbing paper prepared from crushed pulp and a thin layer comprising scattered powder of carboxymethylcellulose (CMC) of an amount of about 1 g per piece of the sanitary napkin, inserted between the above-mentioned two sheets of water-absorbing paper, (3) a film 3 for preventing the leakage of the blood, prepared by forming a mixture of polyvinyl alcohol of a degree of saponification of 93 mol% and 25% by weight of glycerol as a plasticizer into a thin film of 0.02 mm in thickness and (4) a sheet 4 of processed paper obtained by a conventional water-repelling treatment of a sheet of paper made of crushed pulp to an extend not to lose its water-dispersibility were laminated in the above-mentioned order, and the whole body of the above-prepared pile was covered by a non-woven cloth prepared from a mixture of pulp containing short fibers of viscose rayon and a water-soluble resin as a binder to be a shape of a sanitary napkin weighing 7 g.

EXAMPLE 2

As is shown in FIG. 2, (1) a layer 11 for absorbing the menstrural blood, obtained by piling up sheets of water-absorbing paper made of crushed pulp, (2) a layer 12 for absorbing and holding the blood, prepared by the procedures described in Example 1 except for using powdery grafted starch with β-hydroxy ethylacrylate instead of powdery CMC, (3) a similar sheet 14 of processed paper so that which was used in Example 1 and (4) a film 13 of a thickness of 0.02 mm for preventing the leakage of the blood, prepared by formulating a mixture of polyvinyl alcohol of a degree of saponification of 93 mol%, 25% by weight of glycerol as a plasticizer and 0.5% by weight of polyoxyethylene alkyl phenyl ether as a surfactant were piled up in the above-mentioned order, and the whole body of the pile was covered with a sheet of non-woven cloth similar to that used in Example 1 to obtain a sanitary napkin weighing 7 g.

EXAMPLE 3

As is shown in FIG. 3, (1) a layer 21 for absorbing the menstrural blood, prepared by piling up sheets of water-absorbing paper made of crushed pulp, (2) a layer 22 for absorbing and holding the blood, prepared by the same procedures as in Example 1 except for using powdery hydrophilic grafted starch with β-hydroxy ethylacrylate instead of using powdery CMC, (3) a layer 21' for absorbing the blood, which is the same as the layer 21, (4) a film 21 for preventing the leakage of the blood obtained by formulating a mixture of polyvinyl alcohol of a degree of saponification of 90 mol% and 25% by weight of glycerol into a film of thickness of 0.02 mm and (5) the same sheet of processed paper as in Example 1 were piled up in the above-mentioned order. Then the whole piled body was covered with the same sheet of non-woven cloth as that used in Example 1 to prepare a sanitary napkin weighing 8 g.

EXAMPLE 4

As is shown in FIG. 4, a sanitary napkin was formulated by the same procedures as described in Example 1 except for using a layer of 3 mm in thickness for absorbing and holding the menstrural blood, prepared by formulating a mixture of crushed pulp admixtured with uniformly dispersed powder of CMC thereinto. The weight of one piece of the thus prepared sanitary napkin was 7 g.

EXAMPLE 5

As is shown in FIG. 5, (1) a thin layer 8 comprising floss of rayon, (2) a layer 41 for absorbing the menstrural blood, formulated with crushed pulp into a thickness of 3 mm, (3) a layer 42 for absorbing and holding the blood, formulated with a mixture of crushed pulp, powdery CMC and powdery $H_3BO_3$ (using about 1 g of CMC and about 0.1 g of $H_3BO_3$ per piece of the sanitary napkin, the product), (4) a film 43 of 0.02 mm in thickness for preventing the leakage of the blood, prepared by formulating a mixture of polyvinyl alcohol of a degree of saponification of 88.3 mol%, 10% by weight of dextrin and 25% by weight of glycerol and (5) the same sheet of processed paper 44 as that used in Example 1 were piled up in the above-mentioned order, and then the whole body of the thus prepared pile was covered by the same sheet of non-woven cloth as that used in Example 1 to obtain a sanitary napkin. The weight of one piece of the thus prepared napkin was 7 g.

EXAMPLE 6

As is shown in FIG. 6, (1) a thin layer 8 comprising floss of rayon, (2) an absorbing layer for the menstrural blood, formulated into a thickness of 2 mm from crushed pulp, (3) a layer 52 of a thickness of 2 mm for absorbing and holding the blood, prepared by formulating a mixture of crushed pulp, powdery CMC and powdery $Na_2SO_4$ which have been admixed by scattering the powdery materials onto the crushed pulp (the amounts of CMC and of $Na_2SO_4$ were, respectively about 1 g and 0.2 g per piece of the sanitary napkin, the product), (4) the same layer 51' as the layer 51, for absorbing the blood, (5) a film 53 of 0.02 mm in thickness for preventing the leakage of the blood, prepared by formulating a mixture of polyvinyl alcohol of a degree of saponification of 88.3 mol% and 20% by weight of triethylene glycol and (4) the same sheet of processed paper as that used in Example 1 were piled up in the above-mentioned order. The whole body of the thus prepared pile was covered by the same sheet of non-woven cloth as that used in Example 1 to be a sanitary napkin of an unit weight of 8 g.

EXAMPLE 7

As is shown in FIG. 7, (1) a layer 61 for absorbing the menstrural blood, prepared by formulating crushed pulp into a layer of 2 mm in thickness, (2) a layer 62 for absorbing and holding the blood, of a thickness of 2 mm, prepared by formulating a mixture comprising dispersing 0.5 g per piece of sanitary napkin, the product, of cross-linked starch onto crushed pulp, (3) the same layer 61' for absorbing the blood as the layer 61. (4) the same layer 62' for absorbing and holding the blood as the layer 62, (5) a film 63 of 0.02 mm in thickness for preventing the leakage of the blood prepared by formulating a mixture comprising polyvinyl alcohol of a degree of saponification of 89.5 mol% and 20% by weight of sorbitol and (6) the same sheet 64 of processed paper as that used in Example 1 were piled up in the above-mentioned order, and then the whole body of piles thus prepared was covered by the same sheet of non-woven cloth as that used in Example 1 to be sanitary napkin, the unit weight of one piece of the sanitary napkin being 8 g.

In the next place, the test results of examination carried on the sanitary napkins shown in the above-mentioned Examples are illustrated in Table.

In addition, as Comparative Example 1, a sanitary napkin prepared by the same procedures as those described in Example 1 except for not using CMC was used, and as Comparative Example 2, a sanitary napkin of 8 g in unit weight prepared by at first arranging a film of 0.018 mm in thickness of low-density polyethylene and a water-proofing paper on the under surface of an absorbing layer comprising by formulating a mixture of crushed pulp and sanitary cotton into a layer of 8 mm in thickness and by covering the whole body of the thus prepared pile with a conventional sheet of non-woven cloth was used in the same kind of determination of their performances as above.

The methods for comparative experiments on the performances of sanitary napkins are as follows:

(1) Amount of Water Absorbed into an Unit Piece of Sanitary Napkin

A specimen of sanitary napkin is placed on a piece of wire netting of a mesh size of 1,680 microns (corresponding to 10 mesh) and of a known weight with the contact-surface upward (contact-surface means the surface brought into contact with the skin in use), and water is poured onto the whole surface of the specimen gently to make the whole specimen absorb water, and after continuing the pouring until the water overflows the specimen and leaving the specimen as it goes for one minute, the amount of water absorbed in the specimen is determined.

(2) Degree of Prevention of the Exudation and the Leakage of Blood

A specimen of sanitary napkin is placed on a sheet of filter paper which is extendedly placed on a glass plate, with the contact-surface upward, and after a pointed tip of a burrete containing an aqueous Congo red solution obtained by dissolving 0.2 g of Congo red into 100 ml of water (hereinafter referred to as a Congo red solution) is brought into light contact with the center part of the specimen, 10 ml of the solution are poured onto the specimen from the burrete at a rate of 5 to 10 ml/min. After leaving to stand still for one minute, a load of 3 kg having a diameter of 50 mm is applied to determin the time period until the Congo red solution is exuded through the specimen onto the sheet of filter paper. The preventing property of the specimen against exudation and leakage is represented by the above-mentioned time period.

(3) Self-Disintegrability

Figure 8:
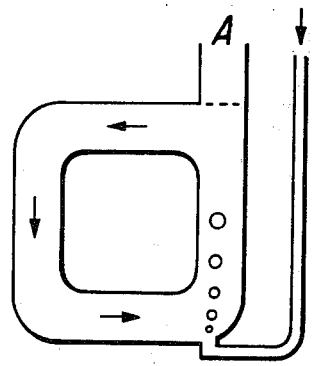
FIG. 8 is the schematic diagram of an apparatus for testing the disintegrating property in water of a sanitary napkin.

As is shown in FIG. 8, a pipe conduit is prepared with a steel pipe of 70 mm in inner diameter. It is filled with water at a temperature of 20° C., and by blowing a pressured air of 0.2 kg/cm$^2$ at a rate of 15 liters/min into the conduit from an inlet provided at the lower part of the conduit the water in the conduit is circulated. While a specimen of sanitary napkin is inserted into the circulating water in the conduit from the inlet port A to be circulated with water. After 5 min of circulation, the water in the conduit is filtered with a wire netting of 5 mesh to observe whether there are any raw material of the specimen not yet self-disintegrated.

The following Table shows the results of tests according to the above-mentioned methods.

TABLE

Test Results on Water-absorbancy, Degree of prevention of leakage and Disintegradability of Sanitary Napkin

| Specimen | Water-absorbancy (times+) | Prevention of leakage (min) | Disintegradability in circulating flow of water |
|---|---|---|---|
| Specimen prepared in Example 1 | 18.8 | 32 | remaining material not observed |
| Specimen prepared in Example 2 | 21.2 | 45 | remaining material not observed |
| Specimen prepared in Example 3 | 20.0 | 42 | remaining material not observed |
| Specimen prepared in Example 4 | 18.5 | 38 | remaining material not observed |
| Specimen prepared in Example 5 | 19.7 | 60 | remaining material not observed |
| Specimen prepared in Example 6 | 20.4 | 60 | remaining material not observed |
| Specimen prepared in Example 7 | 22.5 | 60 | remaining material not observed |
| Specimen prepared in Comparative Example 1 | 12.1 | 28 | remaining material not observed |
| Specimen prepared in Comparative Example 2 | 12.3 | 22 | remaining material observed |

Note:
+Water-absorbancy is represented by ratio of weight of water absorbed to weight of the specimen.

What is claimed is:

1. A sanitary napkin comprising at least one layer formulated of a water-absorbable substance and at least one layer consisting of a film based on water-soluble or water-dispersible polyvinyl alcohol,
    said water-absorbable substance comprising a powder of a water-soluble of water-dispersible polymeric substance and a powder of a gelatinizing accelerator for polyvinyl alcohol selected from the group consisting of boric acid, sodium borate, sodium surface, magnesium sulfate and aluminum sulfate.

2. The sanitary napkin of claim 1, wherein said layer of water-absorbable substance and said layer of a film based on polyvinyl alcohol are adjacent to one another.

3. The sanitary napkin of claim 1, wherein said polymeric substance is one or more species selected from the group consisting of starch, processed starch, cross-linked starch, starch grafted with acrylic monomer, carboxymethyl cellulose and its cross-linked products, hydrophilic copolymers of acrylic monomers, polyethylene oxide and its cross-linked products, copolymers of vinyl ester and ethylenically unsaturated carboxylic acids and their saponification products, polyvinyl alcohol and its derivatives, and cellulose derivatives.

* * * * *

UNITED STATES PATENT AND TRADEMARK OFFICE
CERTIFICATE OF CORRECTION

PATENT NO. : 4,333,464

DATED : June 8, 1982

INVENTOR(S) : Tadao NAKANO

It is certified that error appears in the above-identified patent and that said Letters Patent is hereby corrected as shown below:

Claim 1, line 6, after "water-soluble" change "of" to

--or--

Claim 1, last line, change "surface" to

--sulfate--

Signed and Sealed this

Twenty-sixth Day of October 1982

[SEAL]

Attest:

GERALD J. MOSSINGHOFF

Attesting Officer

Commissioner of Patents and Trademarks